(12) United States Patent  
Barten et al.

(10) Patent No.: US 8,358,105 B2
(45) Date of Patent: Jan. 22, 2013

(54) RECHARGEABLE GAS-MEASURING SYSTEM

(75) Inventors: Stefan Barten, Lübeck (DE); Volker Kuhn, Stockelsdorf (DE); Andreas Suerig, Krummesse (DE)

(73) Assignee: Dräger Safety AG & Co. KGaA, Lübeck (DE)

( * ) Notice: Subject to any disclaimer, the term of this patent is extended or adjusted under 35 U.S.C. 154(b) by 336 days.

(21) Appl. No.: 12/774,981

(22) Filed: May 6, 2010

(65) Prior Publication Data

US 2011/0006730 A1 Jan. 13, 2011

(30) Foreign Application Priority Data

Jul. 11, 2009 (DE) .......................... 10 2009 032 721

(51) Int. Cl.
*H02J 7/00* (2006.01)
(52) U.S. Cl. ........................................................ 320/108
(58) Field of Classification Search .................... 320/108
See application file for complete search history.

(56) References Cited

U.S. PATENT DOCUMENTS

| | | | |
|---|---|---|---|
| 5,184,500 A * | 2/1993 | Krcma et al. .................. 73/23.2 |
| 6,198,400 B1 | 3/2001 | Church et al. |
| 7,633,263 B2 * | 12/2009 | Toya .............................. 320/108 |
| 2002/0089305 A1 * | 7/2002 | Park et al. ...................... 320/108 |
| 2005/0170520 A1 | 8/2005 | Schur et al. |
| 2008/0024091 A1 | 1/2008 | Yamazaki et al. |

FOREIGN PATENT DOCUMENTS

| | | |
|---|---|---|
| DE | 19719730 C1 | 10/1998 |
| DE | 102005045272 | 4/2007 |
| EP | 0533247 A1 | 3/1993 |
| EP | 1644727 A1 | 4/2006 |
| EP | 1886126 A1 | 2/2008 |
| WO | WO 01/14873 A1 | 3/2001 |
| WO | WO 2005/003756 A1 | 1/2005 |
| WO | WO 2006/130528 | 12/2006 |

* cited by examiner

*Primary Examiner* — Arun Williams
(74) *Attorney, Agent, or Firm* — McGlerw and Tuttle, P.C.

(57) ABSTRACT

The transmission of energy from the base station (3) to the mobile gas-measuring device (2) is carried out reliably and with a high level of safety, even in the presence of explosive gases with a gas-measuring system (1) including a mobile gas-measuring device (2) with a battery unit (6) and with at least one sensor (8, 9, 10, 11) for detecting a gas concentration. A base station (3) for the mobile gas-measuring device (2) is provided as well as an interface (7) for transmitting electric energy from the base station (3) to the battery unit (6) of the mobile gas-measuring device (2). The interface (7) for transmitting electric energy from the base station (3) to the battery unit (6) of the mobile gas-measuring device (2) is designed such that the electric energy is transmitted at least partly in a wireless manner.

20 Claims, 3 Drawing Sheets

RECHARGEABLE GAS-MEASURING SYSTEM

CROSS REFERENCE TO RELATED APPLICATIONS

This application claims the benefit of priority under 35 U.S.C. §119 of German Patent Application DE 10 2009 032 721.5 filed Jul. 11, 2009, the entire contents of which are incorporated herein by reference.

FIELD OF THE INVENTION

The present invention pertains to a gas-measuring system with a mobile gas-measuring device, a battery unit and at least one sensor for detecting a gas concentration and with a base station for the mobile gas-measuring device and with an interface for transmitting electric energy from the base station to the battery unit and to a process for operating such a gas-measuring system.

BACKGROUND OF THE INVENTION

Gas-measuring systems with a mobile gas-measuring device are used in various applications for detecting various harmful gases. For example, mobile gas-measuring devices are necessary for detecting toxic gases for checking safety in industrial chemical processing plants or in fighting fires for the fire service. The mobile gas-measuring device is, in general, in functional connection with a base station. The base station is used to supply the mobile gas-measuring device with electric current and, in addition, for data exchange between the mobile gas-measuring device and the base station. The mobile gas-measuring device is operated either with a non-rechargeable battery or a rechargeable battery.

The battery makes available the electric energy for supplying and operating the mobile gas-measuring device. For charging the batteries of the mobile gas-measuring device, the mobile gas-measuring device has a plug-type connection with corresponding contacts. Furthermore, the base station is provided with corresponding opposite contacts or with an opposite plug-type connection. To charge the mobile gas-measuring device, the mobile gas-measuring device must be placed on a base station and the plug-type connection of the mobile gas-measuring device must be brought into mechanical and electric connection with the opposite plug-type connection of the base station. The mobile gas-measuring device and the base station are used, in general, as a gas-measuring system in a rough environment. As a result, high requirements are imposed on dustproofness and waterproofness as well as the robustness of the plug-type connection and opposite plug-type connection at the mobile gas-measuring device and the base station. Besides, gas-measuring systems are used in areas in which explosive gases may occur. As a result, increased efforts are needed for this plug-type connection and opposite plug-type connection to make it possible to avoid sparking when the contact is made or the contact is abolished between the plug-type connection and the opposite plug-type connection. The plug-type connections and opposite plug-type connections known so far are not, in general, mechanically robust and resistant and, furthermore, they can be cleaned with difficulty only. In addition, corrosion may hinder the transmission of energy from the base station to the mobile gas-measuring device.

DE 10 2005 045 272 A1 shows a gas-measuring system with a mobile measuring device, which comprises sensors for detecting gas concentrations and a first control and computing unit for processing the measured signals delivered from the sensors and means for data transmission. A base station has a bracket for mounting the measuring device, with a power supply unit, with a second control and computing unit for actuating alarm generators arranged in the base station and interfaces for feeding media to be measured to the sensors and for data exchange between the mobile measuring device and the base station. The base station is connected by means of a plug-type connection to the mobile gas-measuring device for supplying the mobile gas-measuring device with energy.

SUMMARY OF THE INVENTION

The object of the present invention is therefore to make available a gas-measuring system and a process for operating a gas-measuring system, in which the energy transmission from the base station to the mobile gas-measuring device can be carried out reliably and with a high level of safety, even in the presence of explosive gases. The gas-measuring system shall be able to be manufactured at a low cost and make possible safer and reliable handling.

This object is accomplished with a gas-measuring system comprising a mobile gas-measuring device with a battery unit and at least one sensor for detecting a gas concentration, a base station for the mobile gas-measuring device, an interface for transmitting electric energy from the base station to the battery unit of the mobile gas-measuring device, wherein the interface for transmitting electric energy from the base station to the battery unit of the mobile gas-measuring device is designed such that the electric energy is transmitted at least partly in a wireless manner.

The electric energy for operating and/or charging the battery unit for the mobile gas-measuring device is thus transmitted in a wireless manner, so that no plug-type connection and opposite plug-type connection are necessary on the mobile gas-measuring device and the base station for the electric energy transmission. A plug-type connection and opposite plug-type connection with corresponding mechanical contacts is thus advantageously unnecessary, so that the drawbacks associated therewith do not occur in the gas-measuring system.

In particular, the electric energy can be transmitted by means of electric induction or electromagnetic waves. In case of transmission of the electric energy by means of electromagnetic waves, a transmitter for electromagnetic waves is provided at the base station and a receiver for the electromagnetic waves is provided at the mobile gas-measuring device. The electromagnetic waves sent by the transmitter are received by the receiver and subsequently converted into electric current.

In another embodiment, the base station is used only to supply the mobile gas-measuring device with electric energy.

In another embodiment, the mobile gas-measuring device comprises a G secondary coil or an electric G secondary conductor and electric current can be induced in the G secondary coil or in the electric G secondary conductor.

In a supplementary embodiment the base station comprises a B primary coil or an electric B primary conductor and the electric current can be induced by means of the B primary coil or the electric B primary conductor in the G secondary coil or in the electric G secondary conductor. An alternating current is sent through the B primary coil, designed, e.g., as a cylinder or toroid coil. The alternating current generates a magnetic field, which induces an alternating electric current in the G secondary coil. This induced alternating electric current is subsequently converted by a rectifier into direct current and is subsequently used to charge the battery unit of the mobile gas-measuring device.

The battery unit of the mobile gas-measuring device can be preferably charged with the induced electric current.

In one variant the gas-measuring system comprises a charging station for the base station and preferably the mobile gas-measuring device.

The charging station preferably comprises an L primary coil or an electric L primary conductor and/or the base station has a B secondary coil or an electric B secondary conductor.

Electric current can be induced in another embodiment by means of the L primary coil or the electric L primary conductor in the B secondary coil or in the B secondary conductor and/or in the G secondary coil or in the electric G secondary conductor. The magnetic field generated by the L primary coil in the charging station can be used to induce electric current in the B secondary coil in the base station and/or in the G secondary coil in the mobile gas-measuring device. Thus, when electric current is induced in the G secondary coil in the mobile gas-measuring device, electric current is thus induced directly by the charging station with the L primary coil in the G secondary coil in the mobile gas-measuring device.

In particular, the electric energy induced in the B secondary coil or in the electric B secondary conductor can be used to operate the B primary coil or for electric B primary conductor. The electric energy induced by the charging station by means of the L primary coil in the secondary coil is thus used indirectly to transmit electric energy to the mobile gas-measuring device with the G secondary coil by electric current being induced in the G secondary coil.

In another embodiment, the electric energy induced in the B secondary coil or in the electric B secondary conductor can be stored in a base station battery unit for operating the B primary coil or for the electric B primary conductor. The electric energy is thus transmitted with a time delay indirectly from the charging station via the base station with the base station battery unit to the mobile gas-measuring device.

In an additional variant, the mobile gas-measuring device and the base station have a data interface for preferably wireless data transmission from the mobile gas-measuring device to the base station and/or vice versa and/or the base station is used to amplify the alarm of the mobile gas-measuring device. The wireless data transmission from the mobile gas-measuring device to the base station and/or vice versa is designed, for example, as a radio link or an infrared interface. If the base station is used to amplify the alarm of the mobile gas-measuring device, the base station is provided with optical and/or acoustic and/or mechanical alarm generators.

A process is provided according to the present invention for operating a gas-measuring system with a mobile gas-measuring device with a battery unit and at least one sensor for detecting a gas concentration and with a base station for the mobile gas-measuring device, wherein electric energy is transmitted from the base station to the mobile gas-measuring device for operating the mobile gas-measuring device, wherein the electric energy is transmitted in a wireless manner.

In another variant the electric energy is transmitted by means of electric induction or electromagnetic waves.

In another embodiment, electric energy is transmitted in a wireless manner from a charging station to the base station and/or to the mobile gas-measuring device for operating the base station and/or the mobile gas-measuring device.

In particular, the presence of the mobile gas-measuring device at the base station and/or the presence of the base station at the charging station is detected and/or the energy transmission is controlled from the base station to the mobile gas-measuring device and/or from the charging station to the base station and/or to the mobile gas-measuring device by means of a control and computing unit, especially a microprocessor system. The presence of the mobile gas-measuring device at the base station and/or the presence of the base station at the charging station can be detected, for example, by means of a Reed contact or a Hall sensor.

An exemplary embodiment of the present invention will be described in more detail below with reference to the attached drawings. The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which preferred embodiments of the invention are illustrated.

DESCRIPTION OF THE PREFERRED EMBODIMENTS

Figure 1:
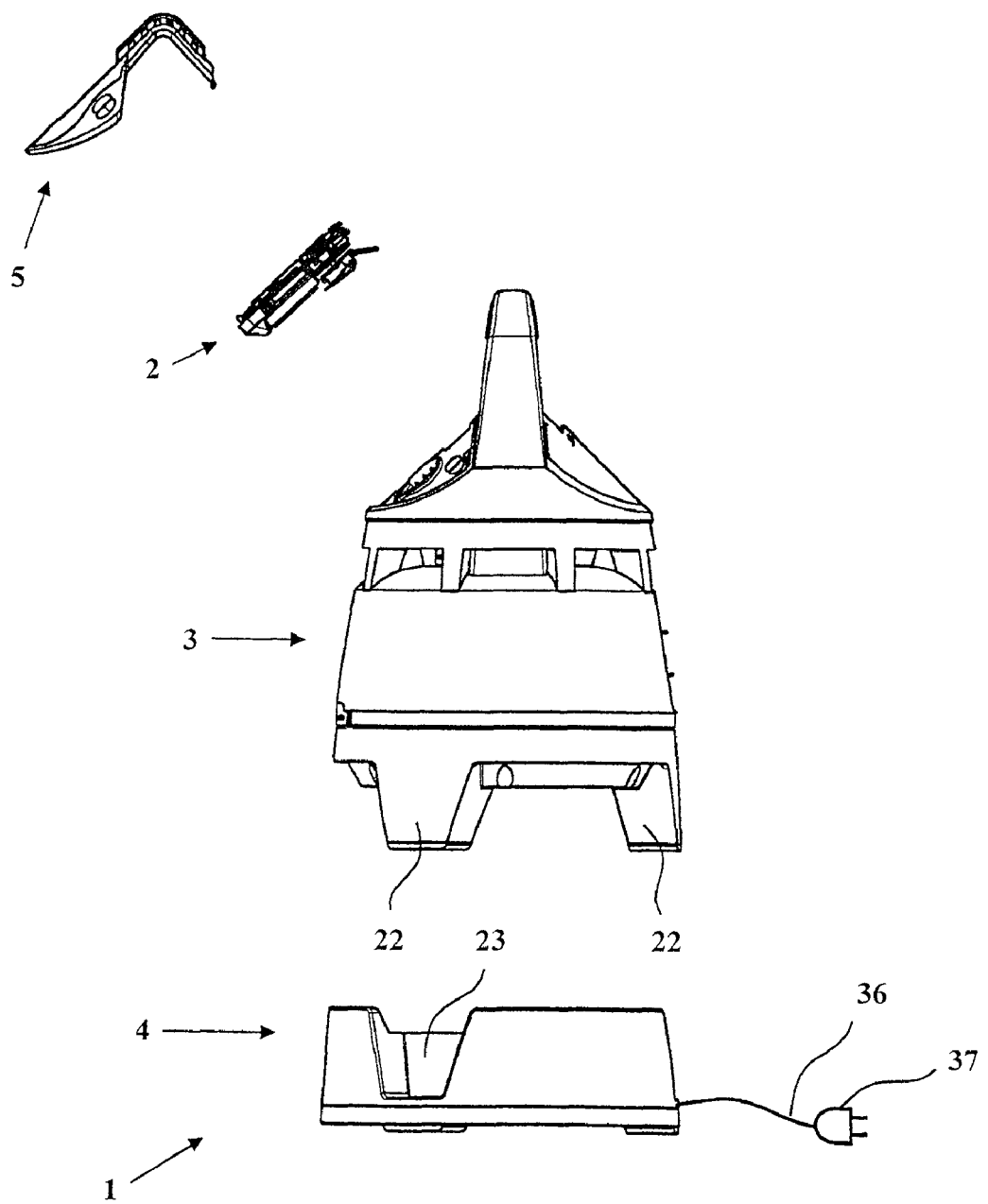
FIG. 1 is a perspective view of a gas-measuring system.

Referring to the drawings in particular, the gas-measuring system 1 with a mobile gas-measuring device 2, a base station 3 and a charging station 4 is used to detect harmful gases. The gas-measuring system 1 is used, for example, in the area of chemical plants or in firefighting by the fire service. The mobile gas-measuring device 2 is portable and can be easily carried by a user of the gas-measuring system 1 during his or her activity.

Base station 3 has legs 22, which can be fitted or inserted into depressions 23 of the charging station 4. The charging station 4 has a power cable 36 as well as a main plug 37 for connection to a power supply unit. The mobile gas-measuring device 2 may be placed on the top side of the base station 3 and subsequently protected by means of a device cover 5 against mechanical damage or contamination while it is placed on the base station 3.

Figure 3:
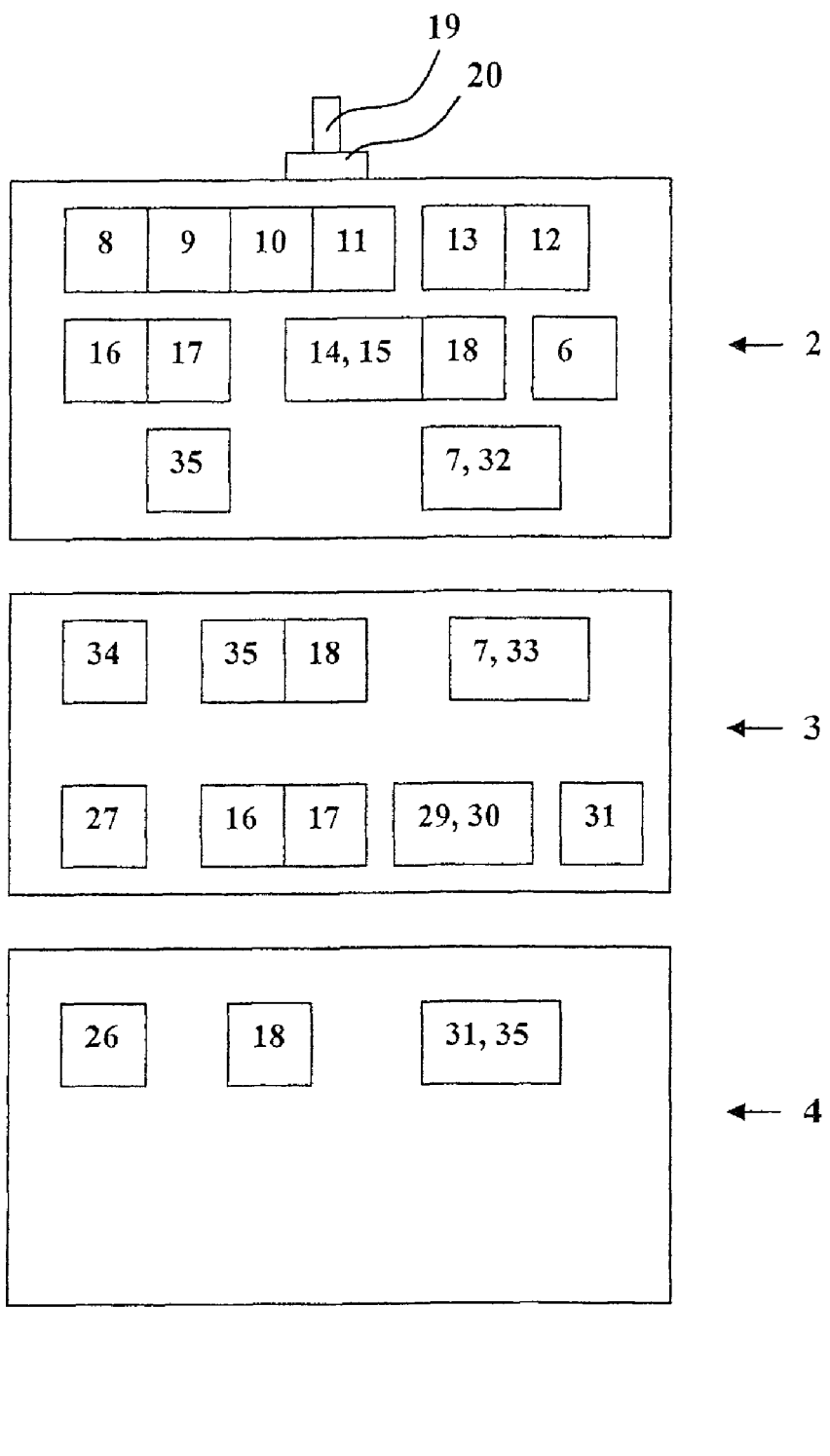
FIG. 3 is a greatly simplified block diagram of the gas-measuring system according to FIG. 1.

The mobile gas-measuring device 2, FIG. 3, has an oxygen sensor 8, a CO sensor 9, an $H_2S$ sensor 10 and a Kat-Ex sensor 11. The concentration of combustible gases can be determined by means of the Kat-Ex sensor 11 by catalytic combustion. The data determined by the sensors 8, 9, 10 and 11 are transmitted by means of electric lines, not shown, to a control and computing unit 12 of the mobile gas-measuring device 2. The control and computing unit 12 analyzes the data determined by the sensors 8, 9, 10 and 11 and sends a warning signal beginning from the point at which certain or predetermined gas concentration values are reached. An optical alarm generator 16 and an acoustic alarm generator 17 as well as a vibrator, not shown, acting as a mechanical alarm generator at the mobile gas-measuring device, are activated for warning by means of the warning signal. To supply the mobile gas-measuring device 2 with energy, said mobile gas-measuring device 2 has a battery unit 6. The gas concentration values determined by the sensors 8, 9, 10 and 11 can be displayed on a display unit 13 at the mobile gas-measuring device 2. Display unit 13 may, furthermore, also be used to display other data, e.g., the state of charge of the battery unit 6. An input unit 14 designed as a keyboard 15 is present at the mobile gas-measuring device 2 for inputting data in the mobile gas-measuring device. For example, the warning or upper limits of the gas concentration values can be entered by means of the keyboard 15.

The mobile gas-measuring device 2 and the base station 3 are provided with a data interface 18 each. The data interface 18 is used for cordless data transmission from the mobile gas-measuring device 2 to the base station 3 and vice versa. This is carried out, for example, by means of a radio link or an infrared interface (not shown). In case of radio link for data transmission from the mobile gas-measuring device 2 to the base station 3 and vice versa, the mobile gas-measuring device 2 is provided with a transmitter and a receiver and the base station 3 is likewise provided with a transmitter and a receiver (not shown). The electromagnetic rays are generated by the transmitter and transmitted to the receiver. As a result, data can be transmitted in a cordless manner. Base station 3 is also used here to amplify the alarm of a warning state triggered by the mobile gas-measuring device 2 or a corresponding warning. The base station is likewise provided for this purpose with an optical and/or acoustic alarm generator as well as preferably also with a mechanical alarm generator 16, 17.

The air to be tested and detected is delivered by means of a pump 20 and a sampling tube 19 to the sensors 8, 9, 10 and 11 in the mobile gas-measuring device 2.

To charge the battery unit 6 of the mobile gas-measuring device 2 the mobile gas-measuring device 2 is to be placed on the top side at a corresponding recess (not shown) of the base station 3. The energy transmission from the base station 3 to the mobile gas-measuring device 2 takes place in a wireless manner by means of electromagnetic induction. An interface 7, for transmitting electric energy from the base station 3 to the mobile gas-measuring device 2, includes a B primary coil 33 in the base station 3 and a G secondary coil 32 in the mobile gas-measuring device 2. An alternating electric current is sent through the B primary coil 33, so that the magnetic field generated by the alternating electric current in the B primary coil 33 in the G secondary coil 32 in the mobile gas-measuring device induces an alternating electric current. This alternating electric current induced in the G secondary coil 32 is converted into direct current by means of an electric rectifier, not shown, and subsequently used to charge the battery unit 6 of the mobile gas-measuring device 2. Thus, no plug-type connection and opposite plug-type connection are advantageously necessary at the mobile gas-measuring device 2 and at the base station 3 for transmitting electric energy from the base station 3 to the mobile gas-measuring device 2.

Figure 2:
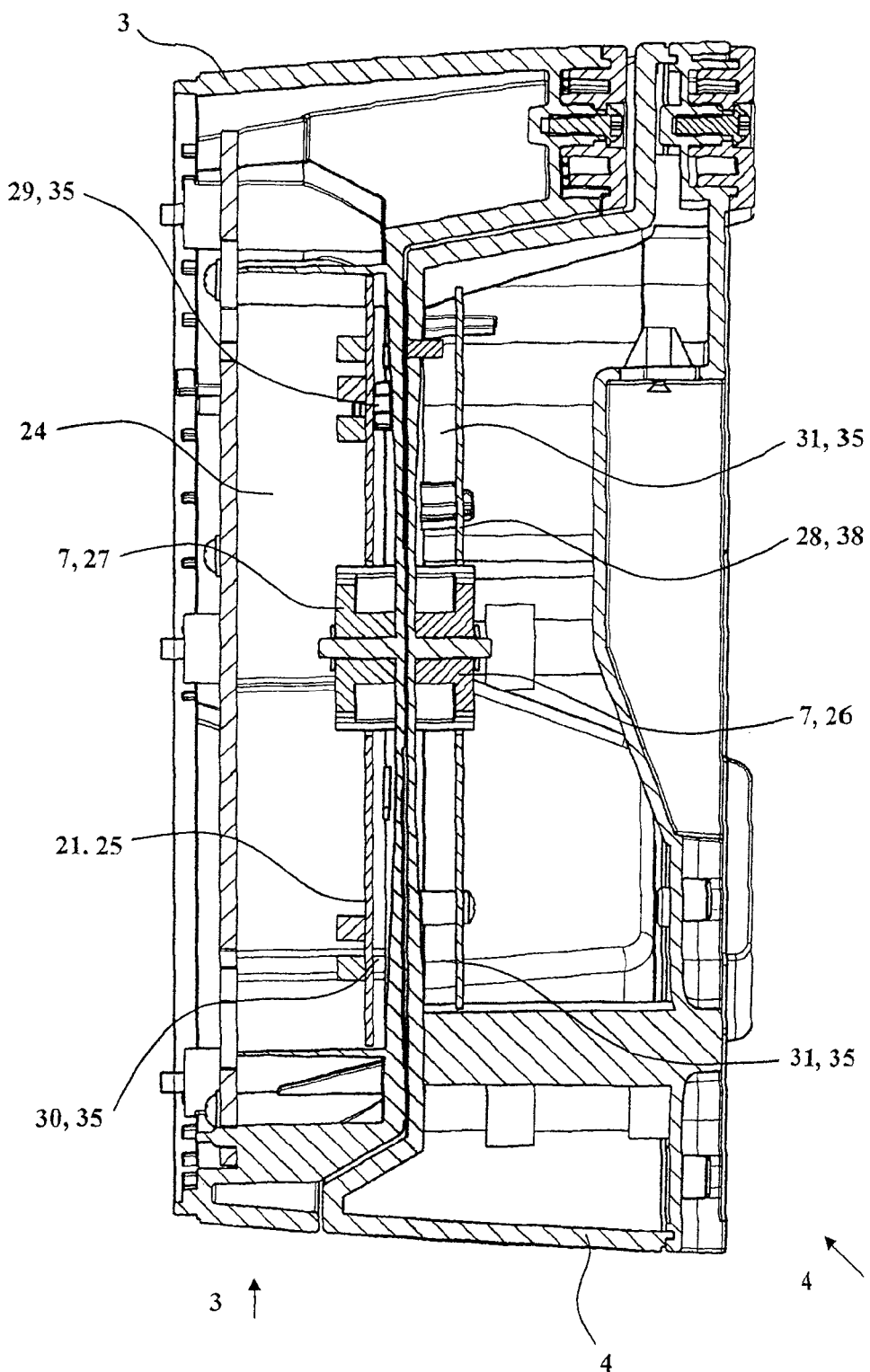
FIG. 2 is a longitudinal sectional view of a charging station and of a base station of the gas-measuring system according to FIG. 1.

Base station 3 has a base station battery unit 34. Furthermore, the charging station 4 is provided with an L primary coil 26 and the base station 3 is provided with a B secondary coil 27. Electric current, which is introduced through the power cable 36 into the charging station 4, is sent through the L primary coil 26 as an alternating current, so that a magnetic field generated by the L primary coil 26 induces an alternating electric current in the B secondary coil 27. This induced alternating electric current is subsequently rectified and the base station battery unit 34 is charged with it. The base station battery unit 34 makes available the electric energy for the B primary coil 33 (not shown in FIG. 2). The electric energy for the mobile gas-measuring device 2 is thus transmitted by the base station 3 indirectly from the charging station 4 to the mobile gas-measuring device 2. Contrary to this, the electric energy can also be transmitted directly from the charging station 4 to the mobile gas-measuring device 2 by corresponding coils (not shown). The L primary coil 26 is to be arranged for this in the immediate vicinity of the G secondary coil 32.

Base station 3 and the charging station 4 are provided with a device 35 for detecting the presence of the base station 3 at the charging station 4. Base station 3 with a bottom plate 24 has for this a first magnet 29 and a second magnet 30. Corresponding to this, two Reed contacts 31 are present at the charging station 4. With the base station 3 placed on the charging station 4, i.e., when the legs 22 of the base station 3 are located in the depressions 23 of the charging station 4, the magnetic field made available by the magnets 29, 30 closes contact tongues, not shown, of the Reed contacts 31, so that there is an electric connection at the Reed contacts 31. When the base station 3 is removed from the charging station 4, this electric connection is not present. A printed circuit board 28 at the charging station 4 with a microprocessor system represents a control and computing unit 38 of the charging station 4. The electric power supply for the L primary coil 26 is released by the control and computing unit 38 when the base station 3 is present at the charging station 4.

This electric power supply is again switched off when the base station 3 is removed from the charging station 4. The control and computing unit 38 of the charging station 4 thus controls the inductive energy transmission from the charging station 4 to the base station 3. A printed circuit board 25 at the base station 3 forms a control and computing unit 21 as a microprocessor system of the base station 3. A device 35 for detecting the presence of the mobile gas-measuring device 2 at the base station 3 is also designed at the mobile gas-measuring device 2 and at the base station 3 analogously to the design of a device 35 for detecting the presence of the base station 3 at the charging station 4 between the base station 3 and the charging station 4. The control and computing unit 21 controls the inductive energy transmission from the base station 3 to the mobile gas-measuring device 2 in an analogous manner. Electric current is transmitted inductively from the base station 3 into the mobile gas-measuring device 2 only when the mobile gas-measuring device is present at or lies on the base station 3. The B primary coil 33 of the base station 3 is supplied with electric current only when the mobile gas-measuring device 2 is present at the base station 3.

The mobile gas-measuring device 2, base station 3 and charging station 4 have the data interface 18 each for the wireless transmission of data from the mobile gas-measuring device to the base station 3 and/or to the charging station 4 and/or vice versa. The wireless data transmission is carried out, for example, by radio or by means of an IR interface. As a result, for example, an alarm generated by the mobile gas-measuring device 2 can be amplified at the base station 3 by corresponding alarm signals being transmitted from the mobile gas-measuring device 2 to the base station 3. The data interface 18 has, in general, a sufficiently wide range, so that the base station 3 can be activated for alarming even in case of a greater distance between the mobile gas-measuring device 2 and the base station 3, e.g., in the range of 2 to 50 m. Moreover, it is also possible, for example, to transmit data on a determined gas concentration curve, on the nature and frequency of alarm and/or on the battery status or state of charge of the battery unit 6 in the mobile gas-measuring device 2 and the base station battery unit 34 in the base station 3. For example, the inductive energy transmission and the charging of the battery unit 6 as well as of the base station battery unit 34 can be controlled and optimized by means of these data by the control and computing units 12, 21 and/or 38.

On the whole, considerable advantages are associated with the gas-measuring system 1 according to the present invention and with the process according to the present invention for operating the gas-measuring system 1. The energy transmission for charging the battery unit 6 of the mobile gas-measuring device 2 is carried out by means of magnetic induction in a wireless manner. Thus, no mechanical plug-type connectors and opposite plug-type connectors are necessary at the mobile gas-measuring device 2 and the base station 3, so that the drawbacks associated therewith, e.g., sparking as well as contamination of these contacts of the plug-type connections and opposite plug-type connections, can no longer occur.

While specific embodiments of the invention have been described in detail to illustrate the application of the principles of the invention, it will be understood that the invention may be embodied otherwise without departing from such principles.

APPENDIX

List of Reference Numbers

1 Gas-measuring system
2 Mobile gas-measuring device
3 Base station
4 Charging station
5 Device cover
6 Battery unit
7 Interface for transmitting electric energy
8 Oxygen sensor
9 CO sensor
10 $H_2S$ sensor
11 Kat-Ex sensor
12 Control and computing unit of the mobile gas-measuring device
13 Display unit
14 Input unit
15 Keyboard
16 Optimal alarm generator
17 Acoustic alarm generator
18 Data interface
19 Sampling tube
20 Pump
21 Control and computing unit of the base station
22 Legs of the base station
23 Depressions of the charging station
24 Bottom plate of the base station
25 Printed circuit board of the base station
26 L primary coil
27 B secondary coil
28 Printed circuit board of the charging station
29 Magnet in base station
30 Magnet in base station
31 Reed contact
32 G secondary coil
33 B primary coil
34 Base station battery unit
35 Device for detecting the presence of the base station at the charging station
36 Power cable
37 Main plug
38 Control and computing unit of the charging station

What is claimed is:

1. A gas-measuring system comprising:
a mobile gas-measuring device with a battery unit and at least one sensor for detecting a gas concentration;
a base station for the mobile gas-measuring device, said base station having a base station battery unit;
an interface for transmitting electric energy from the base station to the battery unit of the mobile gas-measuring device;
a charging station for wirelessly transmitting electrical energy to the base station battery unit;
a means for sensing a presence of said mobile gas-measuring device on said base station and for sensing a presence of said base station on said charging station, wherein electrical energy is wirelessly transmitted from said charging station to said base station battery unit or from said base station to said mobile gas-measuring device when the presence of the base station on the charging station via said means or the presence of the mobile gas unit on the base station is sensed via said means.

2. A gas-measuring system in accordance with claim 1, wherein the electric energy is transmitted by means of electric induction or electromagnetic waves.

3. A gas-measuring system in accordance with claim 1, wherein the mobile gas-measuring device comprises a G secondary coil or an electric G secondary conductor and electric current is induced in the G secondary coil or in the electric G secondary conductor.

4. A gas-measuring system in accordance with claim 3, wherein the base station comprises a B primary coil or an electric B primary conductor and electric current is induced in the G secondary coil or in the electric G secondary conductor by means of the B primary coil or the electric B primary conductor.

5. A gas-measuring system in accordance with claim 3, wherein the battery unit of the mobile gas-measuring device is charged by means of the induced electric current.

6. A gas-measuring system in accordance with claim 1, wherein the charging station comprises an L primary coil or an electric L primary conductor and/or the base station comprises a B secondary coil or an electric B secondary conductor.

7. A gas-measuring system in accordance with claim 6, wherein electric current can be induced by means of the L primary coil or the electric L primary conductor in the B secondary coil or in the B secondary conductor and/or in the G secondary coil or in the electric G secondary conductor.

8. A gas-measuring system in accordance with claim 6, wherein electric energy induced in the B secondary coil or in the electric B secondary conductor is used to operate a B primary coil or an electric B primary conductor.

9. A gas-measuring system in accordance with claim 8, wherein the electric energy induced in the B secondary coil or in the electric B secondary conductor can be stored in the base station battery unit and the electric energy stored in the base station battery unit can be used to operate the B primary coil or the electric B primary conductor.

10. A gas-measuring system in accordance with claim 1, wherein the mobile gas-measuring device and the base station have a data interface for wireless data transmission from the mobile gas-measuring device to the base station and/or vice versa and/or the base station is used to amplify an alarm of the mobile gas-measuring device.

11. A gas-measuring system in accordance with claim 1, wherein said base station comprises a plurality of legs, said charging station comprising a plurality of depressions and a power cable for connection to a power supply unit, wherein electrical energy is supplied to said battery unit of said base station with at least a portion of each of said legs arranged in one of said depressions.

12. A gas-measuring system in accordance with claim 1, wherein said base station comprises a plurality of legs, said charging station comprising a plurality of depressions and a power cable for connection to a power supply unit, wherein electrical energy is supplied to said base station battery unit via said second wireless electrical flow path portion with at least a portion of each of said legs arranged in one of said depressions.

13. A process for operating a gas-measuring system, the process comprising the steps of:
providing a mobile gas-measuring device with a battery unit and at least one sensor for detecting a gas concentration;
providing a base station for the mobile gas-measuring device, said base station having a base station battery unit;
providing an interface for wirelessly transmitting electrical energy from said base station to said battery unit of said mobile gas-measuring device;
providing a charging station for wirelessly transmitting electrical energy to said base station battery unit;
providing a detecting means for detecting a presence of said mobile gas measuring unit on said base station and for detecting a presence of the base station on said charging station;
providing a control and calculating unit; and
controlling a wireless transmission of electric energy from the base station to the mobile gas-measuring device or from said charging station to said base station via said control and calculating unit when the presence of said mobile gas-measuring device is detected on said base station via said detecting means or when the presence of said base station is detected on said charging station via said detecting means.

14. A process in accordance with claim 13, wherein the electric energy is transmitted by means of electric induction or electromagnetic waves, wherein said control and calculating unit comprises a microprocessor system.

15. A gas-measuring system comprising:
a mobile gas-measuring device comprising a mobile gas-measuring device battery unit and a sensor for detecting a gas concentration;
a base station for the mobile gas-measuring device, said base station comprising a base station battery unit;
an interface for wirelessly transmitting electric energy from the base station to the mobile gas-measuring device battery unit;
a charging station;
a detecting means for detecting whether said mobile gas measuring unit is arranged at said base station and for detecting whether said base station is arranged at said charging station, said base station and said mobile-gas measuring device defining a first wireless electrical flow path portion when said mobile gas-measuring device is arranged at said base station, said charging station and said base station defining a second wireless electrical flow path portion when said base station is arranged at said charging station, wherein electrical energy is one or more of wirelessly delivered to said mobile gas-measuring device from said base station via said first wireless electrical flow path portion when said detecting means detects said mobile gas-measuring device is arranged at said base station and wirelessly delivered to said base station battery unit from said charging station via said second wireless electrical flow path portion when said detecting means detects said base station is arranged at said charging station.

16. A gas-measuring system in accordance with claim 15, wherein the mobile gas-measuring device interface part comprises a G secondary coil or an electric G secondary conductor and electric current is induced in the G secondary coil or in the electric G secondary conductor by the interface part of said base station.

17. A gas-measuring system in accordance with claim 16, wherein the base station interface part comprises a B primary coil or an electric B primary conductor and electric current is induced in the G secondary coil or in the electric G secondary conductor by means of the B primary coil or the electric B primary conductor.

18. A gas-measuring system in accordance with claim 16, wherein the battery unit includes a battery charging device receiving electric energy by means of an induced electric current.

19. A gas-measuring system in accordance with claim 16, wherein the mobile gas-measuring device comprises an L primary coil or an electric L primary conductor and/or the base station comprises a B secondary coil or an electric B secondary conductor, wherein electric current can be induced by means of the L primary coil or the electric L primary conductor in the B secondary coil or in the B secondary conductor and/or in the G secondary coil or in the electric G secondary conductor.

20. A process in accordance with claim 15, wherein said base station comprises a plurality of legs, said charging station comprising a plurality of depressions and a power cable for connection to a power supply unit, wherein electrical energy is supplied to said battery unit of said base station with at least a portion of each of said legs arranged in one of said depressions.

* * * * *